United States Patent
Finn et al.

(10) Patent No.: US 10,870,847 B2
(45) Date of Patent: Dec. 22, 2020

(54) METHODS AND KITS FOR NUCLEIC ACID SAMPLE PREPARATION FOR SEQUENCING

(71) Applicant: ArcherDX, LLC, San Francisco, CA (US)

(72) Inventors: Patrick Finn, Carlsbad, CA (US); Greg Patton, Peabody, MA (US); Hongbo Liu, Malden, MA (US)

(73) Assignee: ArcherDX, LLC, San Francisco, CA (US)

( * ) Notice: Subject to any disclaimer, the term of this patent is extended or adjusted under 35 U.S.C. 154(b) by 74 days.

(21) Appl. No.: 15/945,557

(22) Filed: Apr. 4, 2018

(65) Prior Publication Data

US 2019/0078084 A1    Mar. 14, 2019

Related U.S. Application Data

(63) Continuation of application No. 14/440,099, filed as application No. PCT/US2013/068277 on Nov. 4, 2013, now abandoned.

(60) Provisional application No. 61/721,843, filed on Nov. 2, 2012.

(51) Int. Cl.
| | | |
|---|---|---|
| *C12N 15/10* | (2006.01) | |
| *C12Q 1/6806* | (2018.01) | |
| *C12Q 1/6874* | (2018.01) | |

(52) U.S. Cl.
CPC ....... *C12N 15/1093* (2013.01); *C12Q 1/6806* (2013.01); *C12Q 1/6874* (2013.01)

(58) Field of Classification Search
CPC .................................................. C12N 15/1093
USPC ............................................................ 506/9
See application file for complete search history.

(56) References Cited

U.S. PATENT DOCUMENTS

| | | | | |
|---|---|---|---|---|
| 5,604,098 A | * | 2/1997 | Mead ................... | C12N 9/1007 435/6.12 |
| 2002/0061532 A1 | * | 5/2002 | Adams ................. | C12Q 1/6834 435/6.12 |
| 2005/0164226 A1 | * | 7/2005 | Huang ................. | C12Q 1/6813 435/6.1 |
| 2007/0259348 A1 | * | 11/2007 | Phadke ................ | C12Q 1/6806 435/6.12 |
| 2008/0300142 A1 | * | 12/2008 | Getts .................... | C12Q 1/6837 506/9 |

FOREIGN PATENT DOCUMENTS

WO    WO-2012024658 A2 *    2/2012    ........ B01L 3/502738

* cited by examiner

*Primary Examiner* — Karla A Dines (74) *Attorney, Agent, or Firm* — Wolf, Greenfield & Sacks, P.C.

(57) ABSTRACT

The present disclosure relates to methods and kits for DNA library construction, particularly for consistent and reproducible DNA sequencing.

19 Claims, 6 Drawing Sheets

FIGURE 1

| Sample | Units | % (100-500bp) | % (500-8000bp) | Ratio |
|---|---|---|---|---|
| Liquid Control | 15 | 74 | 25 | 0.34 |
| Lyophilized pellet | 15 | 73 | 25 | 0.34 |
| Lyophilized pellet | 7.5 | 74 | 24 | 0.32 |
| Lyophilized pellet | 3.8 | 73 | 26 | 0.36 |
| Lyophilized pellet | 1.9 | 72 | 27 | 0.38 |
| No Enzyme Control | 0 | 17 | 82 | 4.82 |

FIGURE 2

| Sample | Units* | % (100-500bp) | % (500-8000bp) | Ratio |
|---|---|---|---|---|
| Liquid Control | 15/50 | 9 | 90 | 10.0 |
| Lyophilized pellet | 15/50 | 11 | 89 | 8.1 |
| Lyophilized pellet | 7.5/25 | 12 | 88 | 7.3 |
| Lyophilized pellet | 3.8/12.5 | 14 | 86 | 6.1 |
| Lyophilized pellet | 1.9/6.3 | 18 | 81 | 4.5 |
| No Enzyme Control | 0 | 74 | 25 | 0.34 |

* T4 DNA Pol / T4 PNK

METHODS AND KITS FOR NUCLEIC ACID SAMPLE PREPARATION FOR SEQUENCING

PRIORITY

This Application is a continuation of U.S. application Ser. No. 14/440,099, filed May 1, 2015, entitled "METHODS AND KITS FOR NUCLEIC ACID SAMPLE PREPARATION FOR SEQUENCING", which is a national stage filing under 35 U.S.C. § 371 of PCT International Application Serial No. PCT/US2013/068277, filed Nov. 4, 2013, entitled "METHODS AND KITS FOR NUCLEIC ACID SAMPLE PREPARATION FOR SEQUENCING", which claims priority under 35 USC 119(e) to U.S. Provisional Application Ser. No. 61/721,843, filed Nov. 2, 2012, entitled "METHODS AND KITS FOR NUCLEIC ACID SAMPLE PREPARATION FOR SEQUENCING". The entire contents of these applications are incorporated herein by reference in their entirety.

FIELD OF THE INVENTION

The present disclosure relates to methods and kits for nucleic acid sample preparation, particularly for consistent and reproducible nucleic acid sequencing.

BACKGROUND

For nucleic acid sequencing, high throughput sample preparation products are generally shipped with significant quantities of dry ice (up to 50 lbs) to ensure that the reagents remain active upon receipt at the sequencing facility. Most of the enzymes required for sample preparation for next generation sequencing platforms are derived from mesophilic sources which are more sensitive to broad temperature fluctuations that may be observed during shipping. Even thermophilic sources, although they are more stable to temperature ranges, exhibit residual activities that may cause side reactions during shipping that negatively impact product quality upon receipt by the end user.

There is an unmet need for methods and reagents for high throughput sample preparation for next generation sequencers that are room temperature stable and which provide consistent and reproducible results.

SUMMARY OF THE INVENTION

An object of this disclosure is to develop improved reagents for next generation sequencing library construction. In the various aspects, the invention provides methods and kits for library construction, which employ at least one lyophilized reaction mixture. The process of lyophilization yields a product that is inactive at room temperature until rehydrated with water. As a result of lyophilization the enzymes become essentially immobilized and thus are stable to conditions that would previously have caused significant decrease in enzyme activity. Such a formulation, upon lyophilization, yields a sequencing sample preparation kit that can be shipped under ambient conditions, negating the need for dry or wet ice-containing shipping.

In various embodiments, the invention provides for several advantages, including others that will be apparent from the following detailed disclosure. First, the invention enables simplified shipping that doesn't require coolants. Thus the reaction components and kits described herein can be shipped worldwide at room temperature with the simplest of infrastructure. Storage of the products are simplified and the cost and complexity of freezer validation for clinic applications is eliminated. Second, the invention provides enzyme products that are easier to use because the number of pipetting steps required for sample preparation is decreased by up to 30% compared to existing liquid based methods. Decreasing the number of pipetting steps also reduces the possibility of cross contamination. Third, the invention provides improved consistency across a microtiter plate or a broad number of samples due to consistent reagent dosing. Fourth, the invention provides consistent performance because each reaction can be single use in the lyophilized format. This prevents multiple rounds of freeze thawing of stock liquid solutions (typically stored at −20° C.) which if done incorrectly can yield non-homogenous thawing of the product and thus variation in efficiencies of each step in the sample preparation workflow. Stock liquid solutions also increase the probability of cross contamination. The product according to the embodiments of the invention is room temperature stable and thus doesn't have to be thawed prior to use. Overcoming the need to thaw the solutions shortens sample prep time and will yield more consistent results.

BRIEF DESCRIPTION OF THE FIGURES

FIG. 4-6 illustrate library construction.

DETAILED DESCRIPTION OF THE INVENTION

The present invention provides methods and kits for nucleic acid sample preparation. The methods and kits are useful for DNA library construction, in conjunction with, for example, high throughput DNA sequencing. The methods and kits of the invention in various embodiments provide advantages in stability, convenience, and reproducibility.

In one aspect, the invention provides a method for DNA library construction. The method comprises modifying nucleic acid fragments, and ligating nucleic acid adaptors to the modified nucleic acid fragments. In accordance with the invention, one or more of the reactions are rehydrated from a lyophilized form. In some embodiments, DNA fragments are modified with a polymerase and a polynucleotide kinase in a first reaction mixture sufficient for end repair of the DNA fragments. The end repaired DNA fragments are then contacted with a (3'→5' exo) polymerase in a second reaction mixture sufficient for A-tailing the end-repaired DNA fragments. DNA adaptors are then ligated to the A-tailed. DNA in a third reaction mixture that comprises a nucleic acid ligase. In accordance with the invention, wherein one or more of the first reaction mixture, the second reaction mixture, and the third reaction mixture are rehydrated from a lyophilized form.

In certain embodiments, the method comprises contacting DNA fragments with T4 DNA polymerase and T4 polynucleotide kinase in a first reaction mixture sufficient for end repair of the DNA fragments; then contacting the end repaired DNA fragments with Klenow (3'→5' exo-) in a second reaction mixture sufficient for A-tailing the end-repaired DNA fragments; followed by ligating DNA adaptors to the A-tailed DNA in a third reaction mixture comprising T4 DNA ligase. One or more of the first reaction mixture, the second reaction mixture, and the third reaction mixture are rehydrated from a lyophilized form.

The DNA fragments are generally sheared DNA, which may be produced using any technique, many of which are well known.

In some embodiments, the first reaction mixture is rehydrated from a lyophilized form. The lyophilized form may be powder form, but in some embodiments is a pellet, bead, or sphere. Methods of lyophilizing reagents, including as pellets, beads, or spheres (which as used herein are synonymous terms) are well known. For example, see US 2011/0127294, which is hereby incorporated by reference in its entirety.

The lyophilized form (e.g., lyophilized pellet) for the first reaction mixture can comprise a polymerase and polynucleotide kinase, with other reaction components for end repair of DNA fragments (e.g., as described below). For example, the first reaction mixture may comprise T4 DNA polymerase, T4 DNA polynucleotide kinase, deoxynucleotide triphosphates, a source of magnesium, and a buffer. For example, the first reaction mixture may contain from 0.5 to 20 Units of T4 DNA polymerase and 0.5 to 50 Units of T4 polynucleotide kinase. In exemplary embodiments, the first reaction mixture contains from 1 to 50 Units of T4 DNA polymerase and T4 polynucleotide kinase. The dNTPS, when rehydrated at the reaction volume, may be at a concentration of from about 0.1 mM to about 5 mM, such as about 0.2 mM to 1.0 mM, or about 0.4 mM. The source of magnesium can be $MgCl_2$ at from about 2 mM to about 20 mM, such as about 10 mM. Any appropriate buffering agent may be included, such as TRIS-HCl in some embodiments, and should provide a pH of about 7.0 to 8.0, such as about 7.5. Other reaction components such as ATP (e.g., 0.5 to 5 mM), DTT (about 1 mM), KCl (about 1 to 20 mM), and detergents (e.g., Triton X-100) may also be included.

The rehydrated reaction mixture for the first reaction may be from about 25 μl to about 200 μl, but in some embodiments is about 50 μl to about 100 μl in volume. Where the lyophilized form is a pellet, the pellet may have a diameter of from about 0.3 cm to about 1.0 cm. Such sizes can be obtained by lyophilizing volumes of approximately 15 μl to approximately 300 μl.

The lyophilized first reaction mixture may be provided in a sealed single use reaction tube. Upon use, DNA fragments (e.g., about 1 ng to 10 μg sheared DNA) is added in the desired reaction volume (as described) to the single use reaction tube. The lyophilized reagents are thus suspended in the reaction volume to create a reproducible and consistently performing 1× end repair reaction. Incubation times are not critical, but can be, for example, about 30 minutes at room temperature. The end repaired DNA can be purified by standard protocols for A-tailing.

The second reaction mixture comprises components for A-tailing the end-repaired DNA, such as a 3'→5' exo-polymerase and other required reaction components as described below. In various embodiments, the second reaction mixture is rehydrated from a lyophilized form (such as one or more lyophilized pellets). The second reaction mixture comprises Klenow (3'→5' exo-), a source of magnesium, a source of sodium, dATP, and a buffer. Klenow can be present at from about 1 to 20 Units, and can be present at from 5 to 15 Units in various embodiments. The source of magnesium (e.g., $MgCl_2$) may be present at from about 2 to about 25 mM (e.g., about 10 mM), and the source of sodium (e.g., NaCl) may be present at from about 25 mM to about 100 mM (e.g., 50 mM). Other components such as ATP (e.g., at from 0.1 mM to 5 mM), DTT (about 1 mM) may be included. A suitable buffer such as TRIS-HCl should be included for a pH of about 7.0 to 8.5 (e.g., 7.9).

The rehydrated reaction mixture for the second reaction may be from about 25 μl to about 200 μl, but in some embodiments is about 50 μl to about 100 μl in volume. Where the lyophilized form is a pellet, the pellet may have a diameter of from about 0.3 cm to about 1.0 cm. Such sizes can be obtained by lyophilizing volumes of approximately 20 μl to approximately 300 μl.

The lyophilized second reaction mixture may be provided in a sealed single use reaction tube. Upon use, end repaired DNA is added in the desired reaction volume (as described) to the single use reaction tube. The lyophilized reagents are thus suspended in the reaction volume to create a reproducible and consistently performing 1× A-Tailing reaction. Incubation times are not critical, but can be, for example, about 30 minutes at room temperature. The A-tailed DNA can be purified by standard protocols for adaptor ligation.

The third reaction mixture comprises enzyme and reagents for DNA adaptor ligation, such as a DNA ligase. In various embodiments, the third reaction mixture is rehydrated from lyophilized form. The lyophilized form may be one or more lyophilized pellets. The lyophilized form comprises T4 DNA ligase, a source of magnesium, ATP, and a buffer. For example, the T4 DNA ligase may be present at from 1 Unit to about 3,000 Units. The source of magnesium (e.g., $MgCl_2$) may be present at from about 2 mM to about 20 mM (e.g., 10 mM). ATP may be present at from about 0.1 to about 5 mM (e.g., about 1 mM). Other components such as DTT (e.g., about 1 mM), polyethylene glycol, and a suitable buffer (e.g., TRIS-HCl and pH of from about 7.0 to about 8.0, such as about 7.6) may also be provided. In some embodiments, DNA adaptors are included in the lyophilized form. In some embodiments, DNA adaptors are added with the reaction volume.

The rehydrated reaction mixture for the third reaction may be from about 25 μl to about 200 μl, but in some embodiments is about 50 μl to about 100 μl in volume. Where the lyophilized form is a pellet, the pellet may have a diameter of from about 0.3 cm to about 1.0 cm. Such sizes can be obtained by lyophilizing volumes approximately 15 μl to approximately 300 μl.

The lyophilized third reaction mixture may be provided in a sealed single use reaction tube. Upon use, water optionally comprising DNA adaptors (where not provided with the reaction components) is added in the desired reaction volume (as described) to the single use reaction tube. The lyophilized reagents are thus suspended in the reaction volume to create a reproducible and consistently performing 1× ligation reaction. Incubation times are not critical, but can be, for example, about 15 minutes at room temperature. The ligated DNA can be purified by standard protocols.

In various embodiments, at least two of the first reaction mixture, the second reaction mixture, and the third reaction mixture are rehydrated from lyophilized form. In certain embodiments, each of the first reaction mixture, the second reaction mixture, and the third reaction mixture are rehydrated from lyophilized form.

The enzymes employed in the first, second, and third reaction mixtures, may optionally have one or more amino acid modifications with respect to commercially available enzymes (e.g., as available from Enzymatics, New England BioLabs, Inc., or Life Technologies). These modifications can provide various advantages regarding enhancing activity, reducing undesirable side reactions, stability, accuracy, etc. Generally, each enzyme may have from 1 to 20 amino acid modifications selected from (collectively) insertions, deletions, substitutions, truncations, or additions with respect to known or commercially available enzymes. For example, one or more of the T4 DNA polymerase, T4 polynucleotide kinase, klenow (3'→5' exo-), and T4 DNA ligase may have from 1 to 20 amino acid modifications selected from (collectively) insertions, deletions, substitutions, truncations, or additions, such as from 1 to 15, 1 to 10, or 1 to 5 of such modifications in various embodiments.

In a second aspect, the invention provides a kit for DNA library construction. The kit comprises a reaction tube containing first reaction components for end repair of DNA fragments (the DNA fragment need not be included among the first reaction components); a reaction tube containing second reaction components for A-tailing of end-repaired DNA fragments; and a reaction tube containing third reaction components for ligating DNA adaptors to A-tailed DNA. One, two, or each of the first reaction components, the second reaction components, and the third reaction components are in lyophilized form.

The lyophilized form (e.g., lyophilized pellet) for the first reaction mixture can comprise a DNA polymerase. (e.g., T4 DNA polymerase), a DNA polynucleotide kinase (e.g., T4 DNA polynucleotide kinase), deoxynucleotide triphosphates, a source of magnesium, ATP and a buffer. For example, the lyophilized form may contain from 0.5 to 20 Units of T4 DNA polymerase and 0.5 to 50 Units of T4 polynucleotide kinase. The dNTPS, when rehydrated at the reaction volume (as described), may be at a concentration of from about 0.1 mM to about 5 mM, such as about 0.2 mM to 0.6 mM, or about 0.4 mM. The source of magnesium can be $MgCl_2$ at from about 2 mM to about 20 mM, such as about 10 mM. Any appropriate buffering agent may be included, such as TRIS-HCl in some embodiments, and should provide for a pH of about 7.0 to 8.0, such as about 7.5. Other reaction components such as ATP (e.g., 0.5 to 5 mM), DTT (about 1 mM), KCl (about 1 to 20 mM), and detergents (e.g., Triton X-100) may also be included in the first reaction mixture.

The second reaction mixture comprises a 3'→5' exo-polymerase (e.g., Klenow), a source of magnesium, a source of sodium, dATP, and a buffer. Klenow can be present at from about 1 to 20 Units, and can be present at from 5 to 15 Units in various embodiments. The source of magnesium (e.g., $MgCl_2$) when rehydrated at the reaction volume (as described) may be present at from about 2 to about 25 mM (e.g., about 10 mM), and the source of sodium (e.g., NaCl) may be present at from about 25 mM to about 100 mM (e.g., 50 mM). Other components such as ATP (e.g., at from 0.1 mM to 1 mM), DTT (about 1 mM) may be included in the second reaction mixture. A suitable buffer such as TRIS-HCl should be included for a pH of about 7.0 to 8.5 (e.g., 7.9) when rehydrated.

The third reaction mixture comprises enzyme and reagents for DNA adaptor ligation. The lyophilized form comprises a DNA ligase T4 DNA ligase), a source of magnesium, ATP, and a buffer. For example, the T4 DNA ligase may be present at from 1 Unit to about 3,000 Units. The source of magnesium (e,g., $MgCl_2$) when rehydrated at the reaction volume (as described) may be present at from about 2 mM to about 20 mM (e.g., 10 mM), ATP may be present at from about 0.1 to about 5 mM (e.g., about 1 mM). Other components such as DTT (e.g., about 1 mM), polyethylene glycol, and a suitable buffer (e,g., TRIS-HCl pro- viding for a pH of from about 7.0 to about 8.0, such as about 7.6) may also be provided. In some embodiments, DNA adaptors are included in the lyophilized form. In some embodiments, DNA adaptors are added with the reaction volume.

EXAMPLES

Example 1

T4 Polynucleotide Kinase

Figure 1:
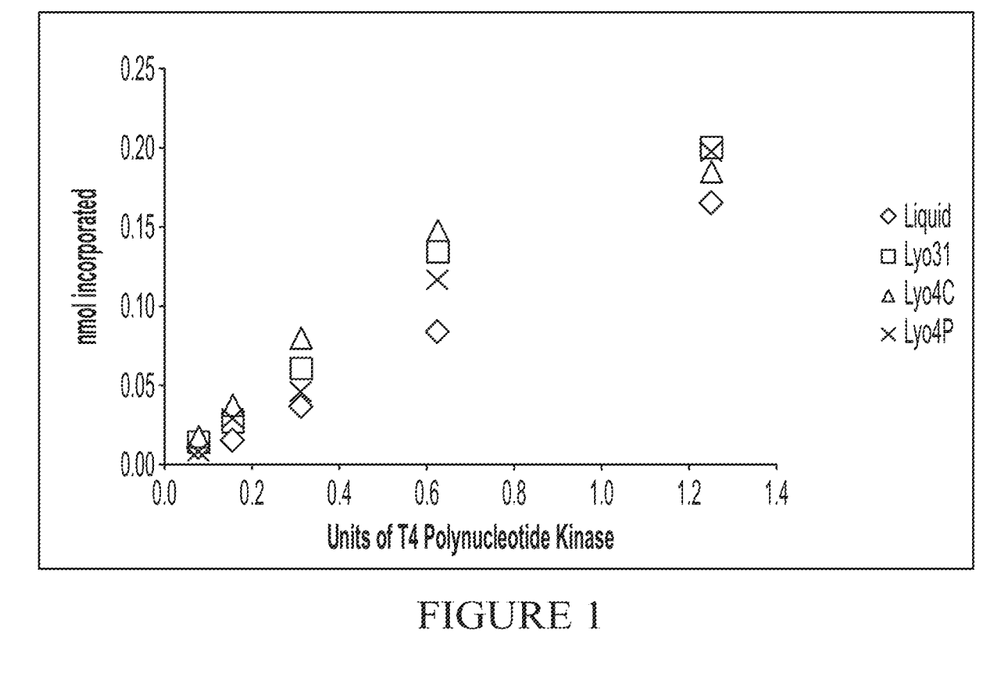
FIG. 1 shows that T4 polynucleotide kinase successfully reactivates its lyophilized format.

FIG. 1 shows that T4 polynucleotide kinase successfully reactivates from its lyophilized format.

Three lyophilized pellet formulations of T4 polynucleotide kinase were treated in foil packs at 50° C. for 2 weeks. The assay measured radiolabeled $\gamma$-$^{32}$P ATP incorporation into poly dT substrate. Activities of all three lyophilized pellet formulations track with a liquid formation stored at −20° C. Two weeks at 50° C. is equal to about 3 months at room temperature.

Example 2

A-Tailing Formulation

Figure 2:
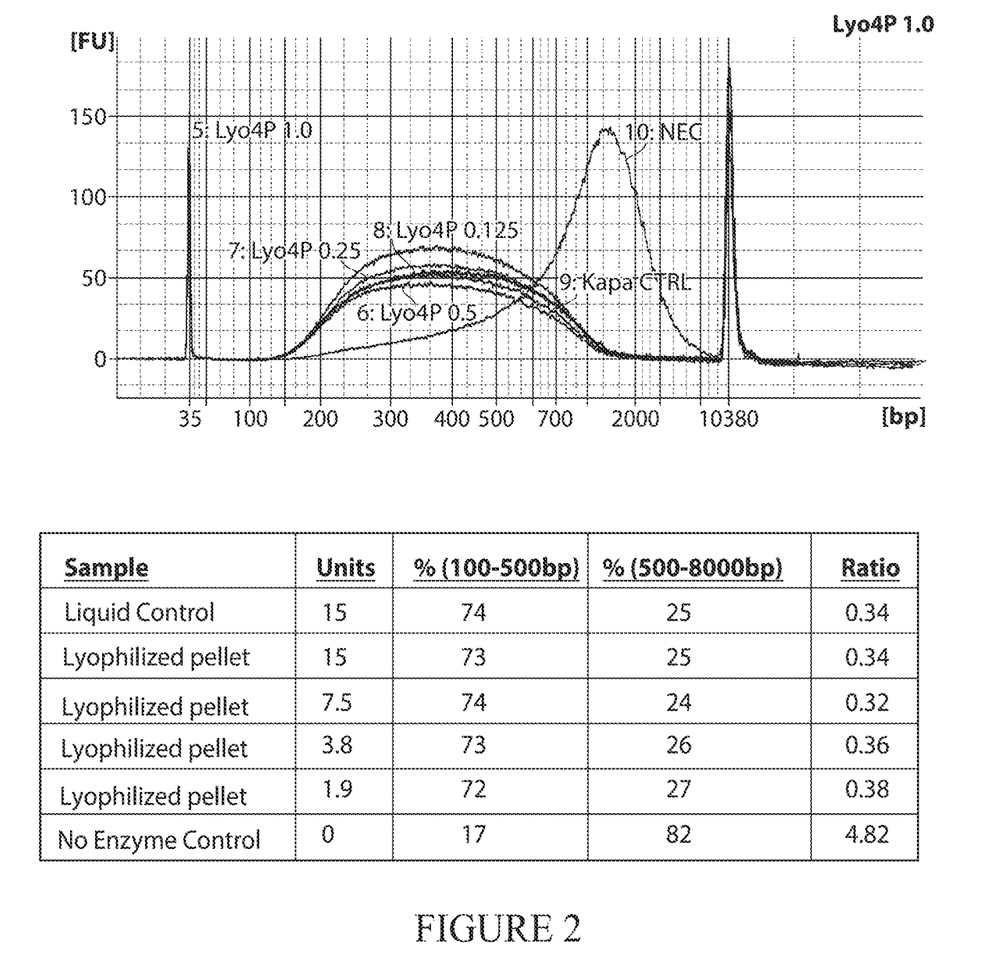
FIG. 2 shows that a lyophilized A-tailing formulation successfully reactivates and performs equivalently to the liquid formulation.

FIG. 2 shows the results of an A-tailing formulation (comprising Klenow Fragment (3'→5' exo-)). DNA was treated with End Repair, and various amounts of Klenow (3'→5' exo-), followed by ligation. Library fragments lacking a 3' A from Klenow (Exo-) are expected to undergo blunt ended ligation. Input of Klenow from 15 Units to 1.9 Units has little effect on the A-Tailing step.

These data show that the lyophilized A-tailing formulation successfully reactivates and perform equivalently to the liquid formulation.

Example 3

End Repair

Figure 3:
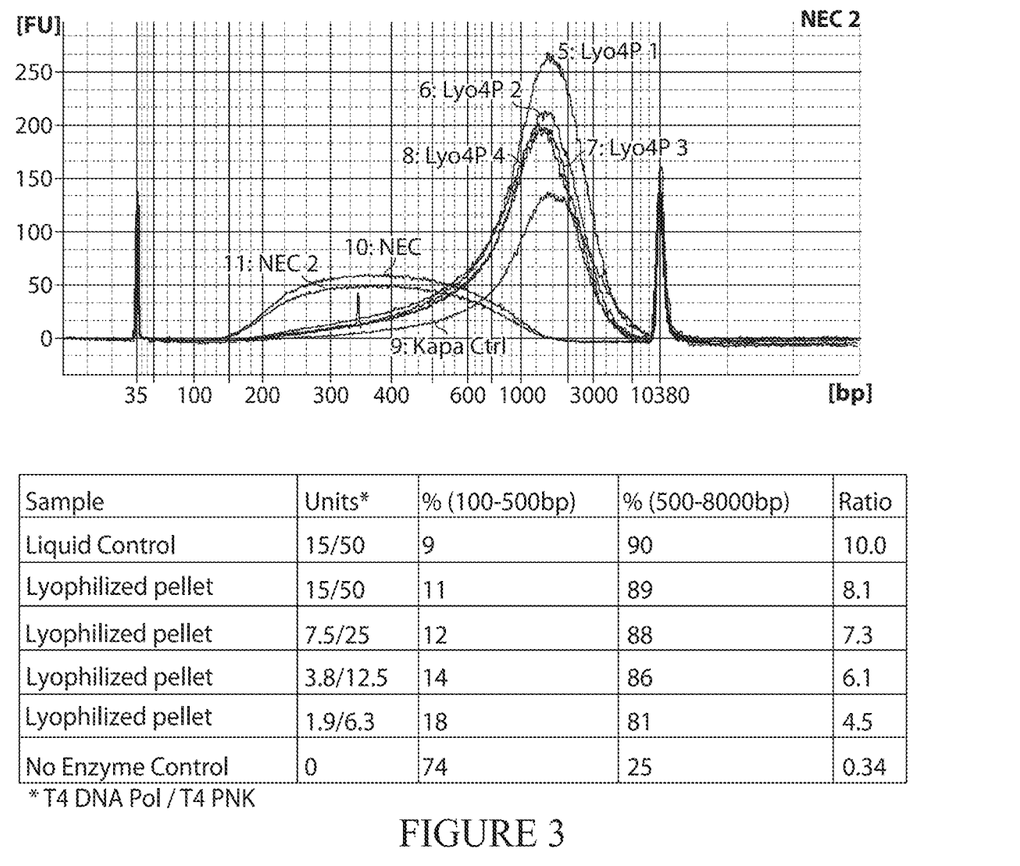
FIG. 3 shows that a lyophilized end repair mix rehydaates and performs equivalently to the liquid reaction mixture.

As shown in FIG. 3, a lyophilized End Repair mix rehydrates and performs equivalently to the liquid reaction mixture. The assay involves treating with various amounts of End Repair and ligation.

Example 4

Library Construction

Figure 4:
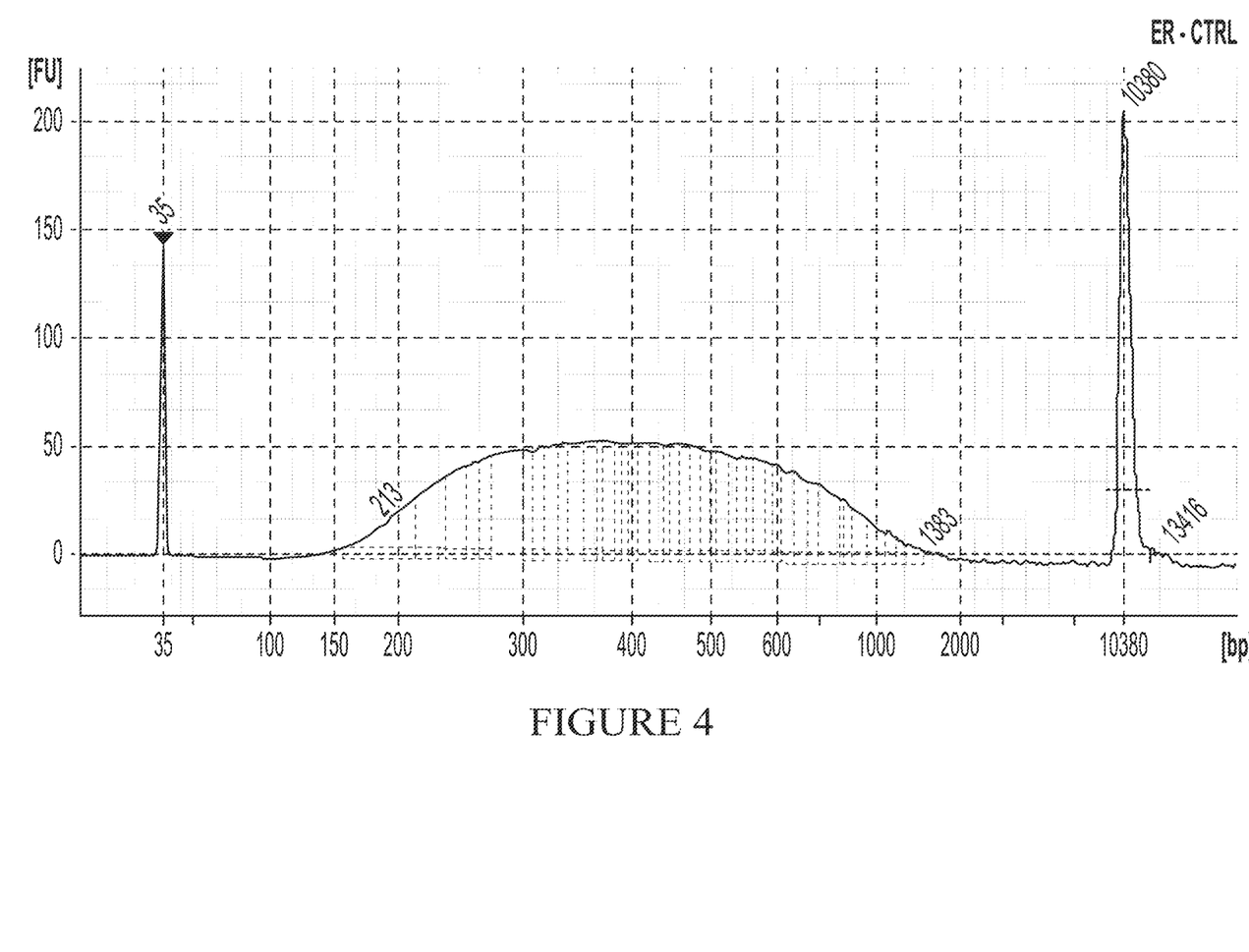
FIG. 4, sheared DNA.
Figure 5:
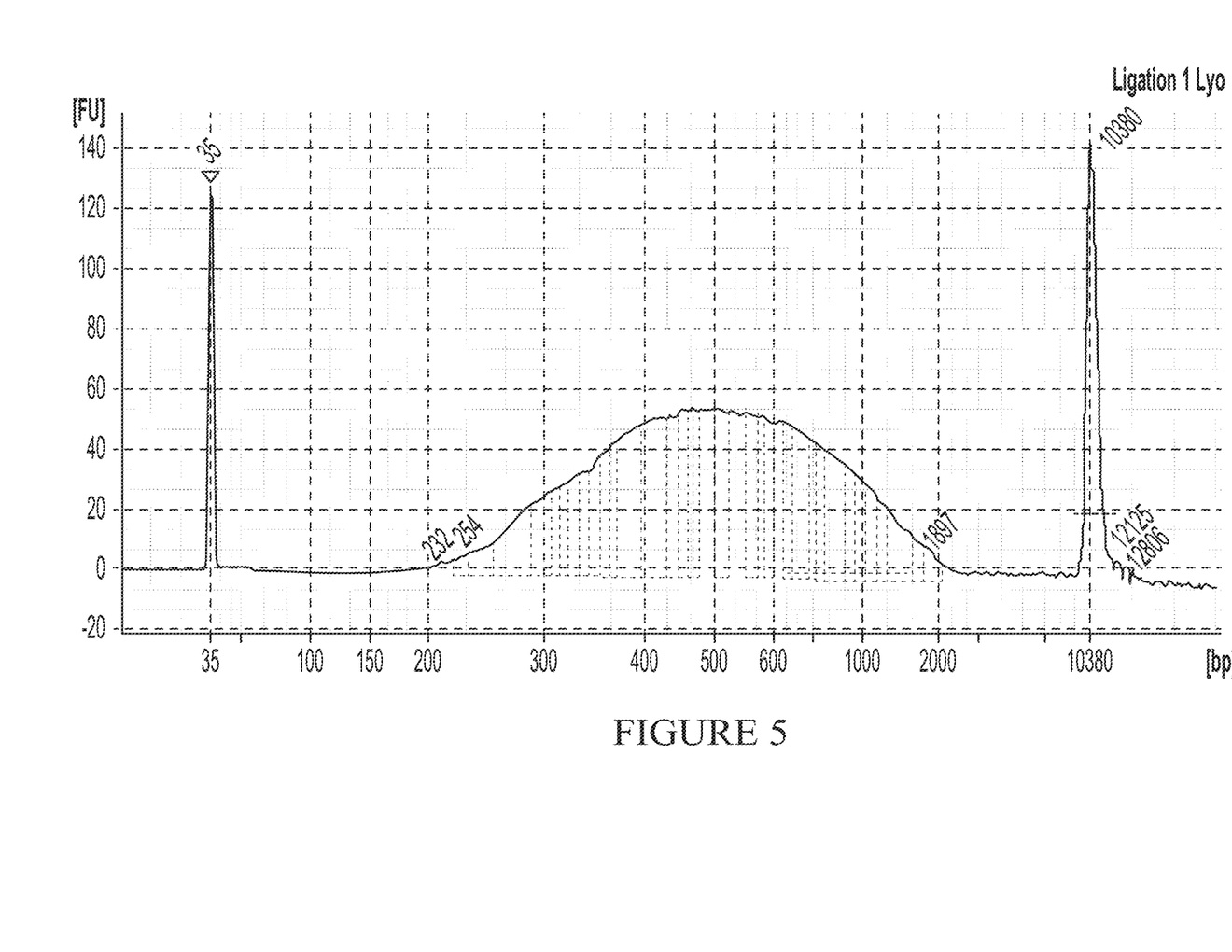
FIG. 5 illustrates the DNA after end repair, A-tailing, and ligation.
Figure 6:
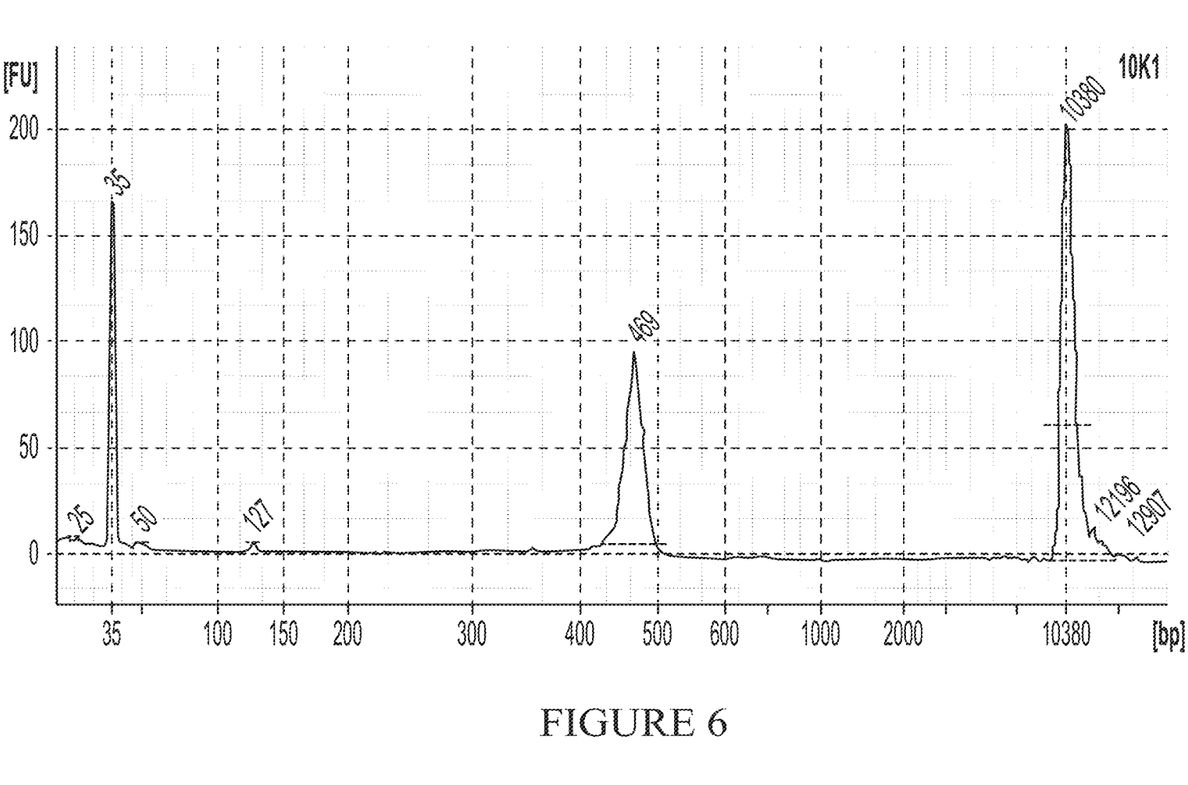
FIG. 6 shows the resulting size selected library.

The traces in FIGS. 4, 5, and 6 show a complete library construction protocol conducted using room temperature stabile reagents.

The starting material was sheared DNA (FIG. 4), which was treated with End Repair, followed by A-tailing and Ligation (FIG. 5).

FIG. 6 shows the size selected library (final library product prior to Amplification).

Exemplary methods for library construction using room temperature stable library construction reagents.

End Repair

Add up to 10 μg sheared dsDNA and water to a final volume of 100 μL to one screw cap tube of lyophilized End Repair reaction. Gently mix to ensure solid dissolves. Incubate for 30 min at room temperature. Purify DNA (AMPure XP Beads, Qiagen MinElute, etc.).

A-Tailing

Add end repaired DNA and water to a final volume of 50 µL to one screw cap tube of lyophilized A-Tailing mix. Gently mix to ensure solid dissolves. Use A-Tailing with End Repair treated DNA or A-Tailing with End Repair treated DNA. Incubate for 30 min at room temperature. Purify.

Ligation

Add A-Tailed DNA, water and DNA adaptors to a final volume of 50 µL to one screw cap tube of lyophilized Ligation mix. Gently Mix to ensure solid dissolves. Incubate for 15 min at room temperature. Purify.

The invention claimed is:

1. A method for DNA library construction, comprising:
   modifying nucleic acid fragments; and
   ligating nucleic acid adaptors to the modified nucleic acid fragments;
   wherein one or more of the reactions are rehydrated from a lyophilized form in a reaction volume comprising the nucleic acid fragments.

2. A method for DNA library construction, comprising:
   modifying DNA fragments with a polymerase and a polynucleotide kinase in a first reaction mixture sufficient for end repair of the DNA fragments;
   contacting the end repaired DNA fragments with a (3'→5' exo-) polymerase in a second reaction mixture sufficient for A-tailing the end-repaired DNA fragments;
   ligating DNA adaptors to the A-tailed DNA fragments in a third reaction mixture comprising a nucleic acid ligase;
   wherein one or more of the first reaction mixture, the second reaction mixture, and the third reaction mixture are rehydrated from a lyophilized form in a reaction volume comprising the DNA fragments.

3. The method of claim 2, wherein at least the first reaction mixture is rehydrated from a lyophilized form.

4. The method of claim 3, wherein the lyophilized form is one or more lyophilized pellets, and wherein each lyophilized pellet has a diameter of from about 0.3 cm to about 1.0 cm.

5. The method of claim 4, wherein the lyophilized pellet is lyophilized from an approximately 15 µl to approximately 300 µl volume.

6. The method of claim 3, wherein the lyophilized form comprises T4 DNA polymerase, T4 DNA polynucleotide kinase, deoxynucleotide triphosphates, a source of magnesium, and a buffer.

7. The method of claim 3, wherein the DNA fragments in the reaction volume are added to a single use reaction tube containing the lyophilized first reaction mixture.

8. The method of claim 2, wherein at least the second reaction mixture is rehydrated from a lyophilized form.

9. The method of claim 8, wherein the lyophilized form is one or more lyophilized pellets, and wherein each lyophilized pellet has a diameter of from about 0.3 cm to about 1.0 cm.

10. The method of claim 9, wherein the lyophilized pellet is lyophilized from an approximately 15 µl to approximately 300 µl volume.

11. The method of claim 8, wherein the lyophilized form comprises Klenow (3'→5' exo-), a source of magnesium, a source of sodium, dATP, and a buffer.

12. The method of claim 8, wherein the end repaired DNA fragments in the reaction volume are added to a single use reaction tube containing the lyophilized second reaction mixture.

13. The method of claim 2, wherein at least the third reaction mixture is rehydrated from a lyophilized form.

14. The method of claim 13, wherein the lyophilized form is one or more lyophilized pellets, and wherein each lyophilized pellet has a diameter of from about 0.3 cm to about 1.0 cm.

15. The method of claim 14, wherein the lyophilized pellet is lyophilized from an approximately 15 µl to approximately 300 µl volume.

16. The method of claim 13, wherein the lyophilized form comprises T4 DNA ligase, a source of magnesium, ATP, and a buffer.

17. The method of claim 13, wherein the A-tailed DNA in the reaction volume are added to a single use reaction tube containing the lyophilized third reaction mixture.

18. The method of claim 2, wherein at least two of the first reaction mixture, second reaction mixture, and third reaction mixture are rehydrated from lyophilized form.

19. A method of for DNA library construction, comprising:
   modifying DNA fragments with T4 DNA polymerase and T4 polynucleotide kinase in a first reaction mixture sufficient for end repair of the DNA fragments;
   contacting the end repaired DNA fragments with Klenow (3'→5' exo-) in a second reaction mixture sufficient for A-tailing the end-repaired DNA fragments;
   ligating DNA adaptors to the A-tailed DNA in a third reaction mixture comprising T4 DNA ligase,
   wherein one or more of the first reaction mixture, the second reaction mixture, and the third reaction mixture are rehydrated from a lyophilized form in a reaction volume comprising the DNA fragments.

* * * * *